United States Patent
Yao et al.

(10) Patent No.: US 9,314,157 B2
(45) Date of Patent: Apr. 19, 2016

(54) DEVICE TO MEASURE PUPILLARY LIGHT REFLEX IN INFANTS AND TODDLERS

(71) Applicants: Gang Yao, Columbia, MO (US); Judith H. Miles, Columbia, MO (US); Dinalankara M. R. Dinalankara, Columbia, MO (US)

(72) Inventors: Gang Yao, Columbia, MO (US); Judith H. Miles, Columbia, MO (US); Dinalankara M. R. Dinalankara, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 355 days.

(21) Appl. No.: 13/848,924

(22) Filed: Mar. 22, 2013

(65) Prior Publication Data

US 2013/0250244 A1 Sep. 26, 2013

Related U.S. Application Data

(60) Provisional application No. 61/685,691, filed on Mar. 22, 2012.

(51) Int. Cl.
| | |
|---|---|
| *A61B 3/14* | (2006.01) |
| *A61B 3/11* | (2006.01) |
| *A61B 5/00* | (2006.01) |
| *A61B 5/16* | (2006.01) |
| *A61B 5/11* | (2006.01) |

(52) U.S. Cl.
CPC ............... *A61B 3/112* (2013.01); *A61B 5/168* (2013.01); *A61B 5/40* (2013.01); *A61B 5/1114* (2013.01); *A61B 5/1128* (2013.01)

(58) Field of Classification Search
CPC ............ A61B 3/10; A61B 3/11; A61B 3/112; A61B 3/14; A61B 3/145
USPC .......... 351/205, 206, 208, 209, 210, 214, 246
See application file for complete search history.

(56) References Cited

U.S. PATENT DOCUMENTS

| 4,789,235 A * | 12/1988 | Borah et al. .................. 351/246 |
|---|---|---|
| 6,322,216 B1 | 11/2001 | Yee et al. |
| 6,714,665 B1 * | 3/2004 | Hanna ..................... G06K 9/00 382/106 |
| 7,665,845 B2 | 2/2010 | Kiderman et al. |
| 7,753,523 B2 | 7/2010 | Kiderman et al. |

(Continued)

FOREIGN PATENT DOCUMENTS

| WO | 2011067788 A2 | 6/2011 |
|---|---|---|
| WO | 2011067788 A3 | 6/2011 |

OTHER PUBLICATIONS

Dynamics of the Pupullary Light Reflex in Unilateral Horner's Syndrome; TEGETMEYER; Ophthalmologe. Feb. 2006; 103 (2): 129-35 (Abstract Only).

(Continued)

*Primary Examiner* — Ricky Mack
*Assistant Examiner* — Robert E Tallman
(74) *Attorney, Agent, or Firm* — Polster Lieder

(57) ABSTRACT

The present disclosure provides a pupillary light reflex (PLR) system, wherein the PLR system includes a remote tracking and imaging system that is structured and operable to generate and acquire high resolution pupil stimulus and response data from a test subject while the test subject is moving and is disposed a distance from remote tracking and imaging system that is greater than or equal to one-third of a meter. The PLR system additionally includes a computer based system controller that is structure and operable to execute PLR software to control the operation of the remote tracking and imaging system and compute PLR information based on the pupil stimulus and response data acquired as the test subject is moving.

12 Claims, 8 Drawing Sheets

(56) References Cited

U.S. PATENT DOCUMENTS

| | | | |
|---|---|---|---|
| 2004/0174496 A1* | 9/2004 | Ji | G06F 3/013 351/209 |
| 2008/0117384 A1* | 5/2008 | Inakagata et al. | 351/243 |
| 2009/0237614 A1* | 9/2009 | Wyatt | 351/205 |
| 2010/0149488 A1 | 6/2010 | Lo et al. | |

OTHER PUBLICATIONS

Infrared Video Pupillometry: A Method Used to Measure the Pupillary Effects of Drugs in Small Laboratory Animals in Real Time; Murray; J Neurosci Methods. Apr. 1981; 3(4); 365-75 (Abstract Only).

Model Control of Image Processing: Pupillometry; Nguyen; Comput Med Imaging Graph. Jan.-Feb. 1993; 17 (1); 21-23 (Abstract Only).

Video Pupil Tracking for Iris Based Identification; Ketchantang; ACIVS 2005, LNCS 3708, pp. 1-8, 2005.

Can Pupil Size and Pupil Responses During Visual Scanning Contribute to the Diagnosis of Autism Spectrum Disorder in Children; Martineau; Journal of Psychiatric Research 45 (2011) 1077-1082 (online article only).

\* cited by examiner

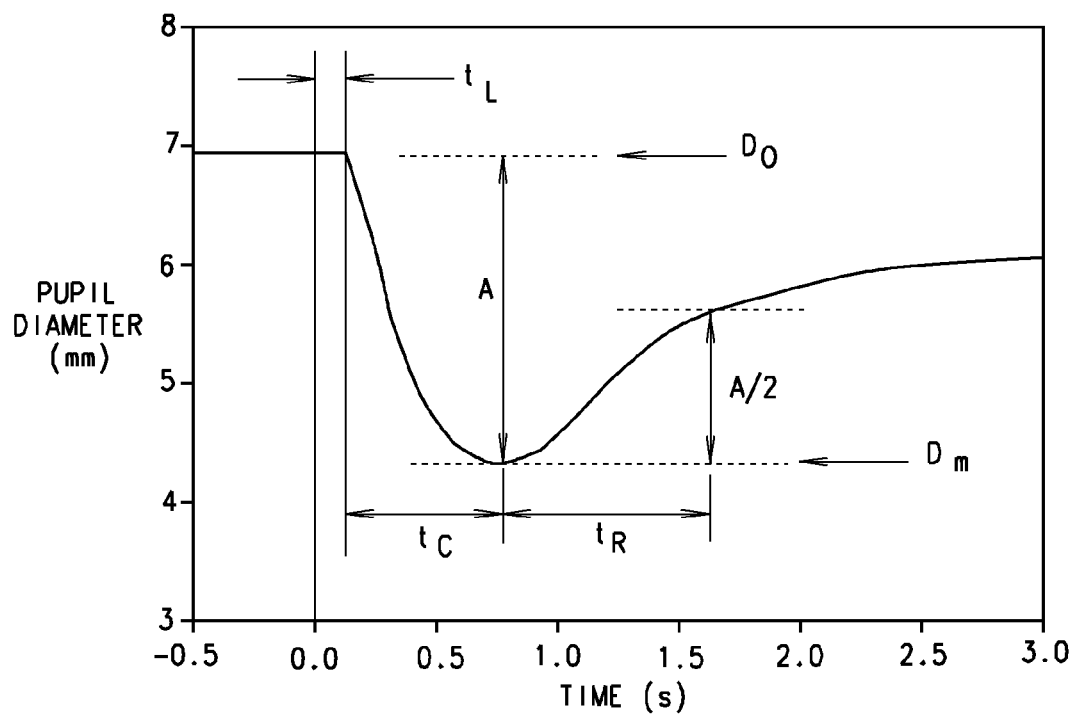
F I G . 1
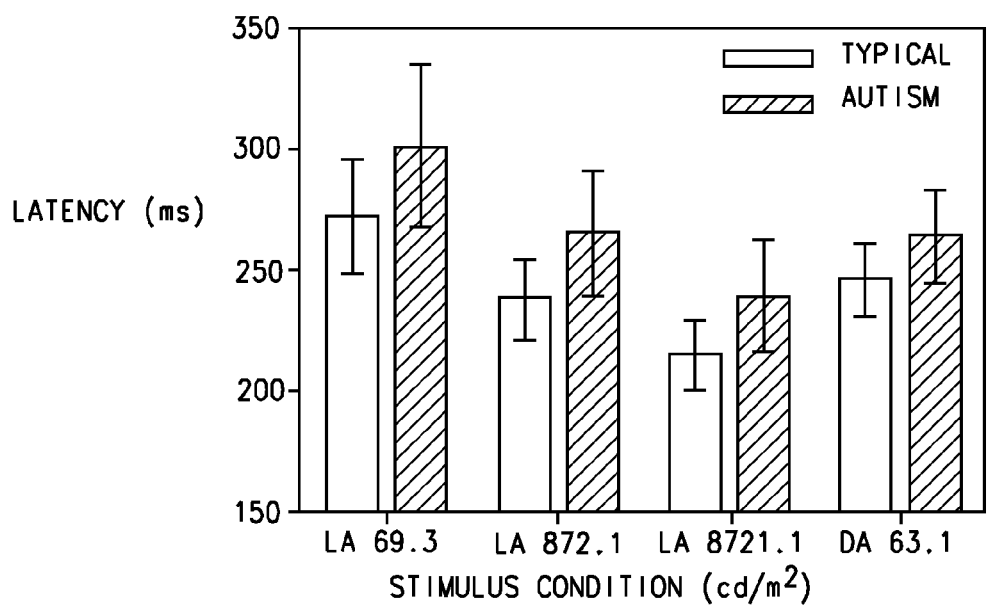
F I G . 2 A

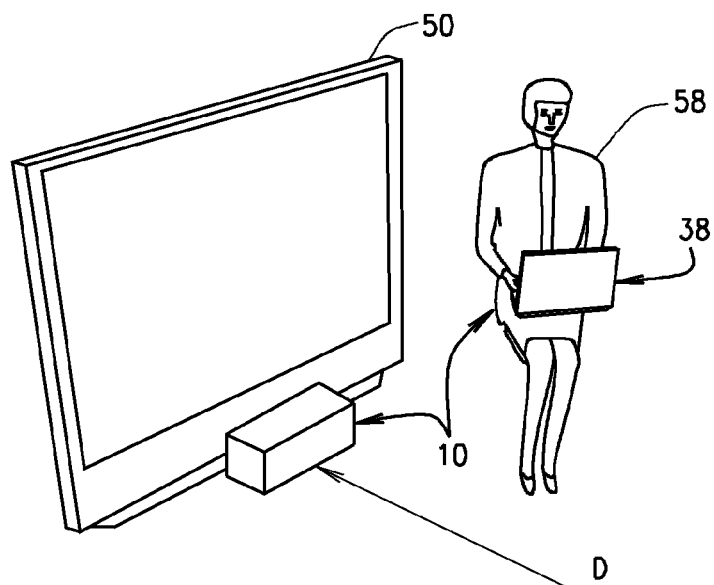
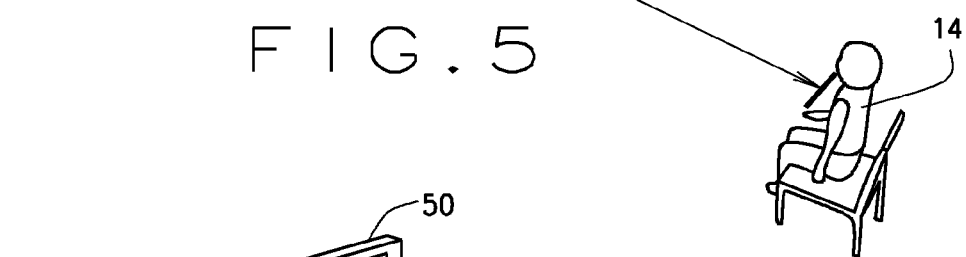
FIG.5
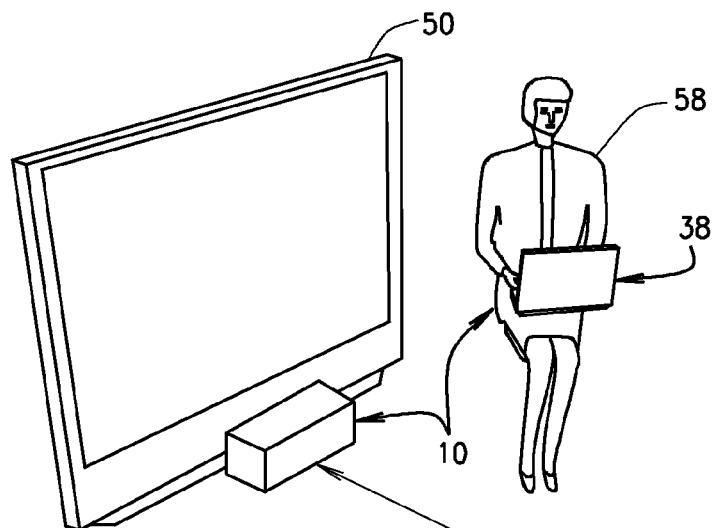
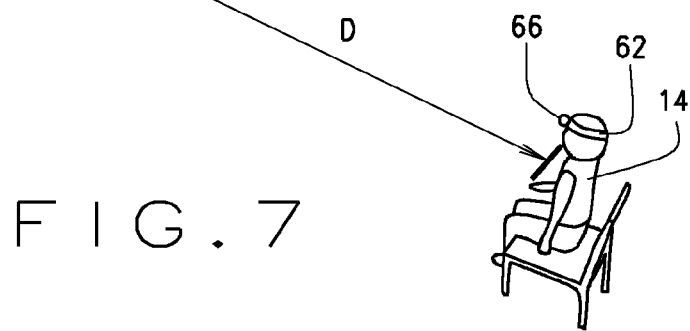
FIG.7

DEVICE TO MEASURE PUPILLARY LIGHT REFLEX IN INFANTS AND TODDLERS

CROSS-REFERENCE TO RELATED APPLICATIONS

This application claims the benefit of U.S. Provisional Application No. 61/685,691, filed on Mar. 22, 2012. The disclosure of the above application is incorporated herein by reference in its entirety.

FIELD

The present teachings relate to an imaging device designed to measure pupillary light reflex in young children, and more particularly to an imaging device that employs imaging techniques to measure reliably the pupillary light reflex in young children who cannot fully cooperate, i.e., remain still, during the examination.

BACKGROUND

The statements in this section merely provide background information related to the present disclosure and may not constitute prior art.

Early identification of children at risk for neurodevelopment disorders is critical for prompt diagnosis and therapeutic interventions. Autism alone develops in 1 in 110 children in U). With more than 25 million 0-5 years old children in US (2011 data), the number of affected children is staggering. Substantial clinical evidence, primarily with children with autism, have proven that early intervention leads to improved functioning including language development, cognitive, social and behavioral remediation. Such improved outcome helps to reduce or eliminate the medical, educational and other special services needed by those affected children throughout their lifetime, which can save "society of $30,000 to $100,000 per child" (Pinto-Martin et al. 2005. Am J Public Health 95:1928). Therefore it has been recognized by all major professional and government agencies (NIH, CDC, AAP, Autism Speaks, etc.) that "early identification of developmental disorders is critical to the well☐being of children and their families" (American Academy of Pediatrics (AAP) Committee on Children with Disabilities 2006).

Current tools for neurodevelopmental screening are typically based on parent reporting, clinical history and observation by specially trained professionals. AAP recommends that all children be screened by their primary care physician at 18 and 24 months using short screening tools such as the PEDS (Parents' Evaluation of Developmental Status) and the MCHAT (Modified Checklist for Autism in Toddlers). Unfortunately, the practice has not been widely adopted; no single tool picks up all children with neurodevelopmental disabilities. As with any human based methods, the accuracy and reliability of such methods are also directly affected by the performer's personal training and experience. In addition, behavioral symptoms usually lag behind the underlying neurophysiological changes. In fact, many children with neurodevelopmental disorders are not detected (AAP Committee on Children with Disabilities 2001, 2006).

Therefore there is a clinical need for an objective measure that can accurately track normal neurodevelopmental progress in infants and toddlers. Such biological (or physical) measures are more precise than behavioral exams and allow early identification of aberrant neurologic development even before behavioral symptoms appear. It is desirable that such tools be easy to use without the need of specially trained operators and be implementable in pediatricians' and family physicians' offices for quick screening of potential risk during the child's preventive visit.

Pupillary Light Reflex (PLR) testing has the potential to meet the clinical need of economic and objective measure to early identification of neurodevelopmental disorder in children. However, it is challenge to use currently available PLR devices (e.g., desktop, handheld or head☐mount devices) in young children because such known devices are placed in close proximity of the eye, which causes unavoidable distractions, especially for infants or children with neurodevelopmental disorders who have heightened sensitivities and limited language. Such distractions often cause the child to close eyes or move the head away in reaction, and can lead to accommodation related pupil size changes ("near response").

SUMMARY

Generally, pupillary light reflex (PLR) is tested by measuring pupil size changes in response to a short light flash. This completely noninvasive test is simple and fast with one test episode taking only a few seconds. Because PLR is an involuntary neurological response and needs minimal cooperation level from the subject, it is ideally positioned for test in young children. Recent experimental studies have shown that PLR is significantly different between children with autism and typically developing children. Most importantly, recent studies suggest that PLR can reveal neurodevelopmental progress in children. All these suggest that PLR has the potential to meet the aforementioned clinical need in early identification of neurodevelopmental disorders.

The present disclosure provides an imaging device designed to measure pupillary light reflex in young children. A "pupillometer" or "pupillography" system refers to the devices that can measure pupillary reactions in response to light stimuli of various intensity and waveforms, which has been widely used in diagnosis of multiple ophthalmological and neurological disorders. Such devices can also be used with other forms of stimuli such as sound, pictures, touch, etc. The present disclosure provides a new and improved device that employs the imaging technique to measure reliably the pupillary light reflex in young children who cannot fully cooperate, i.e., remain still, during the examination.

The imaging system disclosed herein is structured and operable to measure pupillary responses remotely while the subject child naturally fixes his or her eyesight on a given object (e.g. toys or scenic pictures). Additionally, the presently disclosed system is structured and operable to tolerate movement of subject's head while maintaining a tight focus on the pupils, and achieve sufficient temporal and spatial resolution to capture small changes in pupil size. In addition, the imaging system disclosed herein is easy to use and does not require specially trained operators.

An objective of the present disclosure is to provide an imaging system that can accurately measure PLR in young children from a remote distance (e.g., greater than 1 m), and can accommodate test subjects' head movement while maintaining sufficiently high spatial and temporal resolutions.

Another objective of the present disclosure is to provide a remote PLR system with the unique feature of head tracking and auto-focus capability to accommodate child's movement during test.

Another objective of the present disclosure is provide a remote PLR system has sufficient temporal (e.g., <10 ms) and spatial resolution (e.g., <50 μm) to capture small changes in pupil size. Due to such high resolution, a small movement of the head will move the eyes easily out of the imaging area.

In various embodiments, the present disclosure provides a pupillary light reflex (PLR) system, wherein the PLR system includes a remote tracking and imaging system that is structured and operable to generate and acquire high resolution pupil stimulus and response data from a test subject while the test subject is moving and is disposed a distance from remote tracking and imaging system that is greater than or equal to one-third of a meter. The PLR system additionally includes a computer based system controller that is structure and operable to execute PLR software to control the operation of the remote tracking and imaging system and compute PLR information based on the pupil stimulus and response data acquired as the test subject is moving.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 1 is an exemplary graphical Illustration of a pupilogram and extracted pupillary light reflex (PLR) parameters, in accordance with various embodiments of the present disclosure.

FIGS. 2A and 2B is a graphical illustration exemplarily showing PLR latency and relative constriction amplitude in children with autism and with typical development, in accordance with various embodiments of the present disclosure.

FIG. 5 is an isometric diagram of a remote movement immune pupillary light reflex (PLR) system, in accordance with various embodiments of the present disclosure.

FIG. 7 is an isometric diagram of the PLR system shown in FIG. 5, wherein the test subject wears a headband with a small lightweight target attached to enhance and/or simplify a head movement tracking process executed by the PLR system, in accordance with various embodiments of the present disclosure.

Corresponding reference numerals indicate corresponding parts throughout the several views of drawings.

DETAILED DESCRIPTION

Figure 2B:
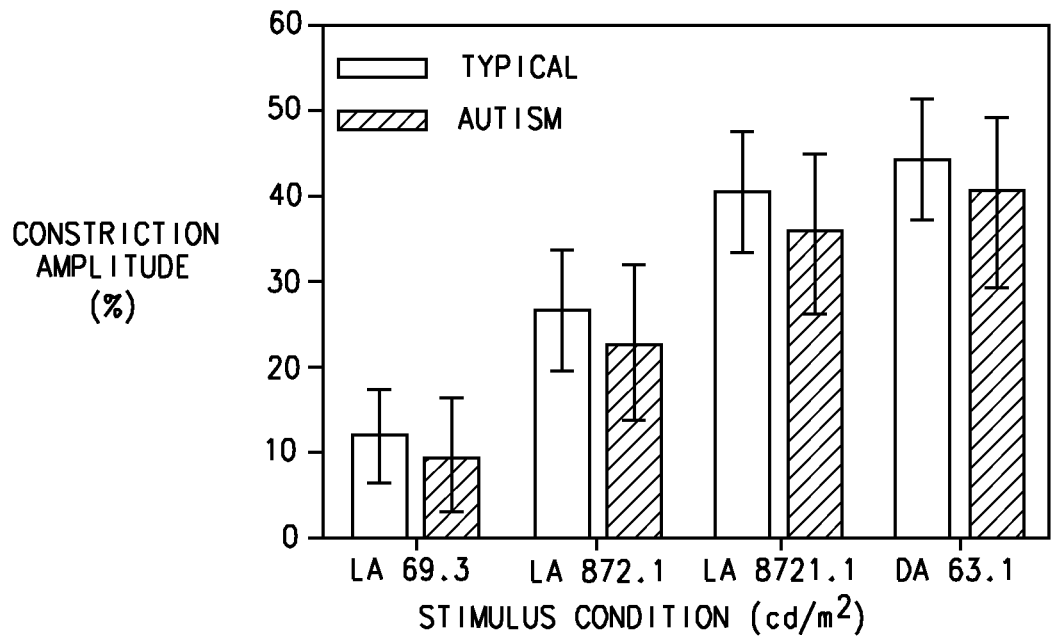

The following description is merely exemplary in nature and is in no way intended to limit the present teachings, application, or uses. Throughout this specification, like reference numerals will be used to refer to like elements.

Devices used for PLR test are generally referred to as "pupillography" devices. Such known PLR have been a popular tool for both basic and clinical investigations in neuro-ophthalmology. Any retinal and brain dysfunctions implicated in PLR pathway alter the PLR responses and thus can be monitored by PLR tests.

Using a conventional desktop pupilometer, PLR testing in a large number of 6-18 years old children, including 154 children with autism and 109 age matched children with typical development, a recent study indicated that children with autism had significantly longer PLR latency (e.g., $p < 0.0001$), smaller PLR constriction (e.g. $p < 0.001$) and shorter constriction time (e.g., $p < 0.0001$) than typical controls. Additionally, the study indicated that these PLR differences were not caused by gender, IQ or medication, and concluded that atypical PLR can be linked to certain neurological dysfunctions in autism. Therefore, due its relative simplicity, PLR can be a valuable model system for studying etiology in autism. As indicated in FIG. 1, multiple PLR parameters can be extracted to quantify a PLR response. In FIG. 1 $t_L$=PLR latency; $t_C$=constriction time; $t_R$=recovery time; $D_0$=initial pupil diameter; $D_m$=the maximal constricted pupil diameter; A=constriction amplitude=$(D_0-D_m)$; and the relative constriction amplitude is computed as the ratio of constriction amplitude and the initial pupil size $(D_0^2-D_m^2)/D_0^2$.

FIG. 2 exemplarily illustrates PLR latency and relative constriction amplitude in children with autism and with typical development. The results were obtained at three light☐adapted (LA) stimulus conditions and one dark☐adapted (DA) condition in 152 children with autism (10.8±3.4 yr) and 109 typically developing children (11.0±2.9 yr). The error bars indicate the standard deviation.

Figure 3:
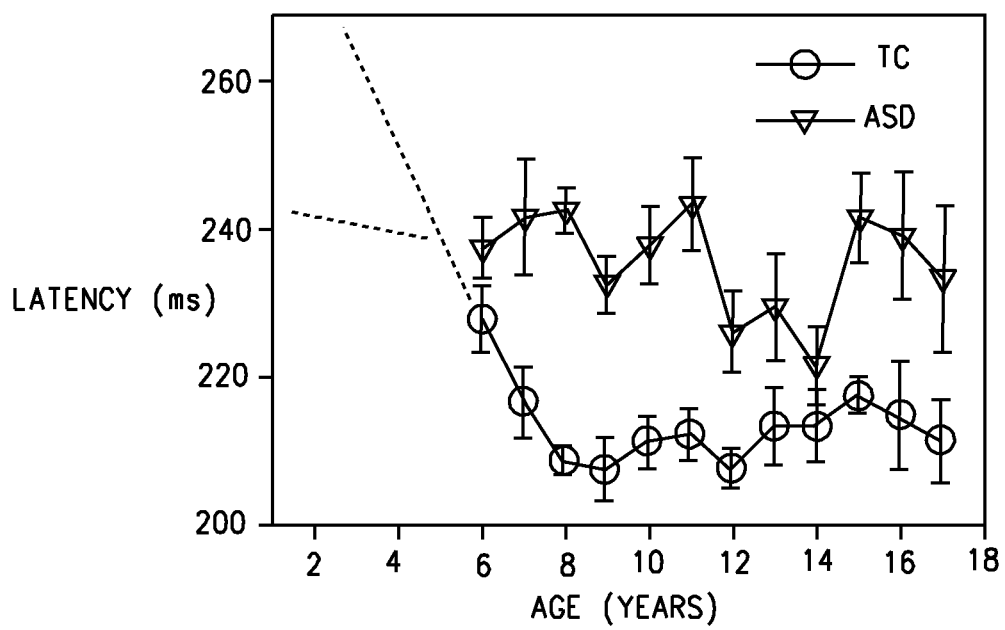
FIG. 3 is a graphical illustration exemplarily showing PLR latency measured in children with autistic spectrum disorder (ASD) and children of typical development, in accordance with various embodiments of the present disclosure.

Interestingly, PLR latency revealed a significantly altered neurodevelopmental trajectory in children with autism. As shown in FIG. 3, the PLR latency decreased significantly from 6 to 8 years old and stabilized thereafter in typical controls. However, no significant age effect was observed in the autism group. In other words, PLR latency findings indicated that a normal neurodevelopmental progression associated with the PLR pathway did not occur in children with ASD.

FIG. 3 exemplarily illustrates PLR latency measured in children with ASD and children of typical development (TC). The results shown were obtained at light-adaption with a stimulus of 8721.1 cd/m2. Similar results were obtained at all other stimulation conditions. The error bars indicate standard error of the mean. Dash lines illustrate the extrapolated trend from experimental data.

Although not being confirmed, it is hypothesize that the aforementioned neurodevelopmental progression begins in infancy or as toddlers based on general understandings of human neurodevelopment. Thus, the difference between children with autism and typical controls will be reversed at younger age. To explore the potential underlying neurological mechanisms, attempts have been to compare the observation with previously reported neurodevelopmental progression obtained using other functional measures.

Figure 4A:
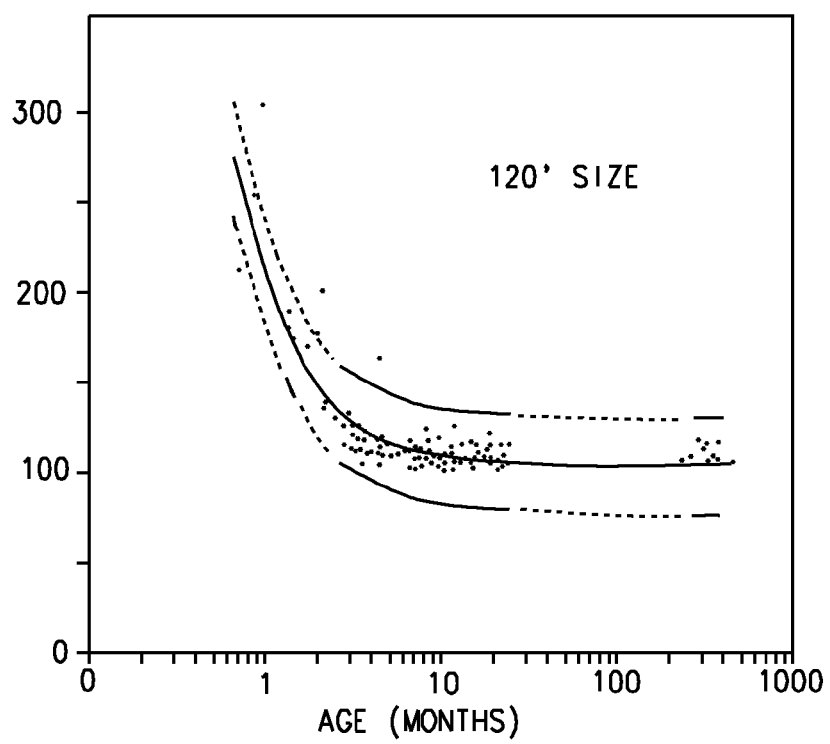
FIG. 4A is a graphical illustration exemplarily showing VEP (visually evoked potential) signal latency, in accordance with various embodiments of the present disclosure.
Figure 4B:
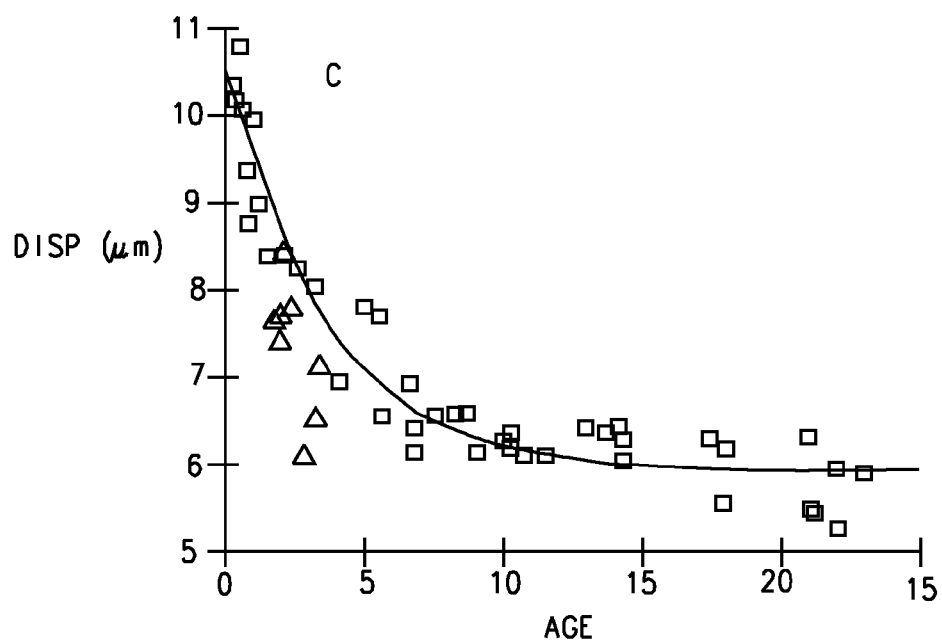
FIG. 4B is a graphical illustration exemplarily showing diffusion tensor magnetic resonance imaging results, in accordance with various embodiments of the present disclosure.

FIG. 4A exemplarily illustrates the VEP (visually evoked potential) signal latency suggesting maturation of visual system in the first year in typical controls (McCulloch, D. L., & Skarf, B. (1991). Development of the human visual system: Monocular and binocular pattern VEP latency. *Investigative Ophthalmology and Visual Science*, 32, 2372-2381). FIG. 4B exemplarily illustrates diffusion tensor magnetic resonance imaging (MRI) results that indicate white matter maturation progress in children (age in "years") (squares=control; triangles=autism) (Bashat, D. B., Kronfeld-Duenias, V., Zachor, D. A., Ekstein, P. M., Hendler, T., Tarrasch, R., Even, A., Levy, Y., & Ben Sira, L. (2007). Accelerated maturation of white matter in young children with autism: A high b value DWI study. *NeuroImage*, 37, 40-47). From FIGS. 4A and 4B, the developmental progress of PLR latency appears to be different from maturation of visual system measured by pattern VEP. However, the developmental progress of PLR latency shares similar age dependence as in white matter maturation revealed in diffusion tensor MRI which reached plateau at ~9 years.

To further indicate the potential link between PLR latency and white matter development, MRI results indicated that white matter maturation is accelerated in children with autism before 4 years old, and the trend is reversed in older children. Such age related cross over in diffusion tensor MRI is in good agreement with the exemplary illustration shown in FIG. 3, suggesting that PLR can be applied to monitor brain development in young children.

Referring now to FIG. 5, the present disclosure provides a remote movement immune pupillary light reflex (PLR) system 10 that can be placed a distance D, i.e., one-third of a meter, one-half of meter or greater, from a test subject 14, e.g., an infant or small child. Moreover, the system 10 can accurately determine pupil latency and other PLR information from the subject 14 from the distance D while the subject 14 is free to move and assume generally any disposition. That is, the system 10 can be placed the distance D from the subject 14 who can be sitting, standing, supine, kneeling, etc., and can move his/her head within a defined field of view while the system 10 continuously monitors the subject's 14 pupils and accurately detects small and rapid changes in the subject's 14 pupils with a high resolution, e.g., a resolution of 50 μm or better.

Figure 6:
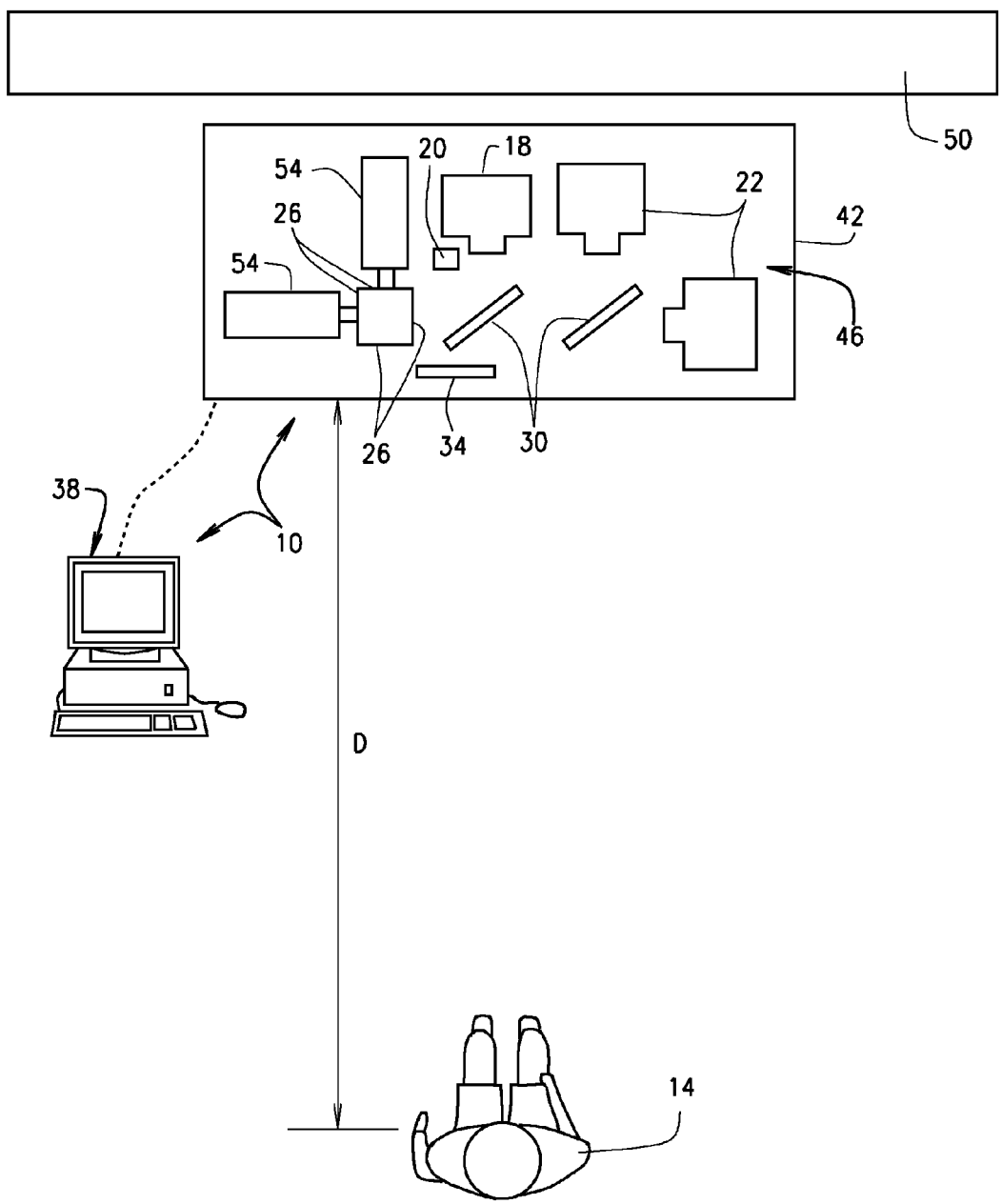
FIG. 6 is a block diagram of the remote movement immune pupillary light reflex (PLR) system shown in FIG. 5, in accordance with various embodiments of the present disclosure.

Referring now to FIGS. 5 and 6, in various embodiments, the system 10 includes a subject movement tracking camera 18, a subject illumination device 20, a least one pupil data acquisition camera 22, a plurality of movable scan mirrors 26, at least two beam splitters 30, an optical stimulation light source 34, and computer based system controller 38. In various embodiments, the tracking camera 18, the subject illumination device 20, the pupil camera(s) 22, the scan mirrors 26, the beam splitters 30 and the optical stimulation light source 34 are arranged within an enclosure 42, e.g., a box approximately 12"×8"×6" or smaller, that is portable enough to fit any environment, and can be installed in any position or orientation to accommodate the disposition of the subject 14. The tracking camera 18, the pupil camera(s) 22, subject illumination device 20, the scan mirrors 26, the beam splitters 30 and the optical stimulation light source 34 will cumulatively be referred to herein as the tracking and imaging system 46.

The system controller 38 is communicatively connected to the tracking and imaging system 46 via a wired or wireless connection and is structured and operable to execute PLR software, i.e., one or more PLR programs and/or algorithms. Execution of the PLR software controls and coordinates the operations of various components of the tracking and imaging system 46 to store subject eye location data, high resolution pupil stimulus and response data, and other PLR data received from the tracking and imaging system 46, and utilizes the received data to accurately compute pupil latency and other PLR information.

To utilize the system 10, the tracking and imaging system 46 is placed in front of an attention stimulus device 50. The attention stimulus device 50 can be any device structured and operable to attract and hold the attention of the subject 14. For example, the attention stimulus device 50 can be a television or computer monitor displaying a movie or other viewable attraction, or any other item or device that will cause the subject to visually focus or fixate on the respective attention stimulus device 50. Subsequently, the subject 14, e.g., a small child, is allowed to assume a comfortable disposition the distance D from the tracking and imaging system 46. For example, the subject 14 is allowed to sit on a chair or on a parent's lap, lay supine on a bed or couch, kneel or sit on the floor, etc. While the subject 14 is comfortably positioned the distance D from the tracking and imaging system 46 the attention stimulus device 50 is operated to attract and hold the attention of the subject 14. While the subject's 14 attention is trained or focused on the attention stimulus device 50, e.g., the subject 14 is visually fixated on the attention stimulus device 50, the PLR system 10 acquires and stores the subject eye location data, high resolution pupil stimulus/response data, and other PLR data, and computes the pupil latency and other PLR information as described below.

In various embodiments, the movement tracking camera 18 can be a charge-coupled device (CCD), e.g., an infrared CCD, or other digital imaging device. The tracking camera 18 is structured and operable to acquire data regarding the general movement of the subject's 14 head and eyes utilizing the subject illumination device 20 as a source of illumination. More particularly, tracking camera 18 is structured and operable to acquire data regarding movement of the position or location of the subject's 14 eyes within the field of view of the tracking camera 18, i.e., the subject eye location data. Hence, the field of view of the tracking camera 18 particularly includes the subject's 14 head and can include more of the subject's 14 body if desired.

The subject illumination device 20 can be any suitable light source that is structured and operable to provide an illumination source for the tracking camera 18 and the pupil camera(s) 22 to which the human eye is not sensitive, particularly a light source to which the human pupil will not be responsive. For example, in various implementations, the subject illumination device 20 can be one or more infrared (IR) light emitting diodes, or other IR light source, generating IR light with a wavelength of approximately 800-900 nm. Additionally, the subject illumination device 20 is disposed within the enclosure 42 such that the light projected by the subject illumination device 20 is off-axis with the line-of-sight between the subject's 14 face and the pupil camera(s) 22, therefore, "black" pupil images (i.e., no "Red Eye" effect) can be acquired by the pupil camera(s) 22, as described below. In various embodiments, the beam splitters 30 are structured and operable to direct a desired portion of the reflected light, i.e., the light from the subject illumination device 20 that is reflected off the subject 14 back to the cameras 18 and 22, toward the tracking camera 18 and a desired portion toward each of the pupil camera(s) 22.

The pupil camera(s) 22 is/are high-resolution CCDs or other high resolution digital imaging devices that are structured and operable to maintain a constant close focus on the subject's 14 pupils and acquire high-resolution pupillary stimulus/response data, e.g., pupillary stimulus/response data having a resolution of 50 μm or better. Particularly, the tracking and imaging system 46 is structured and operable to train the line-of-sight of each pupil camera 22 on a corresponding one of the subject's 14 eyes. For example, the tracking and imaging system 46 will be operated, as described herein, such that a field of view of each pupil camera 22 will cover an imaging area of approximately 3.0 cm×2.0 cm, e.g., approximately 2.0 cm×1.5 cm, and have a line-of-sight directed toward the corresponding one of the subject's 14 eyes. In various embodiments, the pupil camera(s) 22 is/are IR CCDs that have good near-infrared responses, a frame rate of more than 110 fps, e.g., more than 120 fps, and a spatial resolution 50 μm or better.

Importantly, the PLR system 10 is structured and operable to utilizing input from the tracking camera 18 to adjust the line-of-sight between the pupil camera(s) 22 and the subject's 14 pupils, via the scanning mirrors 26, to maintain an on-axis line-of-sight of the subject's 14 pupils even as the subject 14 moves his/her head. More specifically, each of the scanning mirrors 26 is connected to one of a plurality of scan controller 54, e.g., control motors or piezoelectric actuators, that are structured and operable, as controlled by the system controller 38, to adjust the position or angle of the scan mirrors 26 to maintain the on-axis line-of-sight of the pupil camera(s) 22 with subject's 14 pupils.

As described above, the tracking camera 18 monitors the position and movement of the subject's 14 head and communicates the position and movement data, i.e., the subject eye location data, to the system controller 38. The system controller, via execution of the PLR software, utilizes the subject eye location data to adjust the position or angle of the scanning mirrors 26 such that the line-of-sight of the pupil camera(s) 22 with subject's 14 pupils is constantly maintained on-axis as the subject 14 moves his/her head from side-to-side. In various embodiments, the PLR software includes state-of-art eye-tracking and iris biometric programs and algorithms. That is, the system controller 38, via execution of the PLR software, can utilize the position and orientation of the subject's head to correctly calculate the actual pupil size.

For example, if the subject 14 moves backward, the pupil appears smaller, and if the subject 14 rotates his/her head, the pupil image becomes elliptical. Therefore, the measured pupil size can be corrected based on the subject's 14 head position. Or, for example, if the subject's 14 head moves to one side, the subject's 14 pupils will move out of the imaging area, i.e., field of view, of the pupil camera(s) 22. However, the subject's 14 head will still be in the imaging area, i.e., field of view, of the tracking camera 18. Accordingly, via execution of the PLR software and utilization of the real-time subject eye location data streamed from the tracking camera 18 to the system controller 38, the system controller 38 will calculate the current new position of the subject's 14 eyes. Then, based on the calculated new position, the system controller 38 will actuate the scan controllers 54 to adjust the angle/position of the scan mirrors 26 to redirect the line-of-sight pupil camera(s) 22 to be on-axis with the subject's 14 pupils. Hence, the tracking camera 22 continuously tracks the movement of the subject's 14 head and the system controller 38 continuously adjusts the scanning mirrors 26 so that the pupil camera(s) 22 continuously stay on-axis with the subject's 14 pupils, before, during and after the subject 14 moves his/her head.

Generally, to identify the subject's 14 head, both intrinsic face features (such as eye, nose) and external markers can be used. For example, in various embodiments, light emitted from the subject illumination device 20 is reflected from the cornea surface of the subject's 14 eyes and forms a bright point in the acquired eye location data, herein referred to as "glint". Such glint is useful for identify the subject's eye. The relative position of the glint to the tracking and imaging system 46 and the subject's 14 head position is used to determine the subject's 14 gaze direction, which is then used to correct the measured pupil size.

Alternatively, as exemplarily shown in FIG. 7, in various embodiments, to enhance and/or simplify, the head movement tracking process, the subject 14 can wear a headband 62 with a small lightweight target 66 attached. In such embodiments, pattern recognition algorithms of the PLR software will be applied to quickly identify the target 66 and locate its position and track its movement within the field of view of the tracking camera 18. Subsequently, the system controller 38 will adjust the angle/position of the scanning mirrors 26 to maintain the on-axis line-of-sight of the pupil camera(s) 22.

Referring now to FIGS. 5, 6 and 7, in various embodiments, the pupil camera(s) 22 is/are equipped with an auto-focus mechanism to automatically account for front-to-back movement of the subject's 14 head, i.e., movement of the subject's head that changes the distance between the subjects head and the pupil camera(s) 22. Hence, the auto-focus capability of the pupil camera(s) 22 will constantly maintain high resolution focus on the subject's 14 pupils, and the scanning mirrors 26 will be constantly adjusted to constantly maintain an on-axis line-of-sight between the subject's 14 pupils and the pupil camera(s) 22 before, during and after movement of the subject's 14 head. Therefore, the pupil camera(s) 22 can constantly acquire high resolution pupillary stimulation/response data before, during and after movement of the subject's 14 head.

The auto-focus mechanism can be any suitable mechanism structured and operable to automatically monitor the focus of the pupil camera(s) 22 and automatically adjust the focus to constantly maintain a high resolution focus. For example, in various embodiments, the auto-focus mechanism can be a custom telephoto lens comprising a combination of large aperture achromatic positive lens and a small aperture achromatic negative lens in a Barlow configuration. The mechanism can additionally include a small motorized piezoelectric stage will be used to move the negative lens to adjust the effective focal lens of the telephoto lens. Once the object distance is obtained, it is used to calculate the required effective focal length of the telephoto lens, which in turn is used to set a driving signal to the piezoelectric stage.

The optical stimulation light source 34 can be any light source structured and operable to generate light, e.g., white light, red light or green light, that causes pupillary response of the subject's 14 eyes. For example, in various embodiments, the optical stimulation light source 34 can comprise one or more green light emitting diodes, generating light with a wavelength of approximately 500-550 nm, i.e., a wavelength to which the human eye is very sensitive. In various embodiments, the intensity of the optical stimulation light source 34 can be automatically adjusted based on the distance D, using a power meter or other suitable device (not shown), to maintain a consistent level of stimulation.

Activation of the optical stimulation light source 34 is controlled by a system operator 58. Particularly, real-time eye observation data of the subject's 14 eye location is streamed from the pupil camera(s) 22 to the system controller 38, where the data is rendered as images on a display monitor 160 of the system controller 38 for viewing by the system operator 58. When the system operator 58 determines that streamed eye observation data indicates an appropriate time to stimulate the subject's 14 pupils, the system operator 58 selectively activates the optical stimulation light source 34. After which, the system controller 38, via execution of the PLR software, begins acquiring pupil stimulus/response data from the pupil camera(s) 22, as described further below. Hence, the system operator can monitor the subject's visual fixation on the attention stimulus device 50 from the real-time video feed from the pupil camera(s) 22 to the display of the system controller 38 and initiate one or more PLR sequences at selected times, even as the subject 14 moves his/her head.

Figure 8:
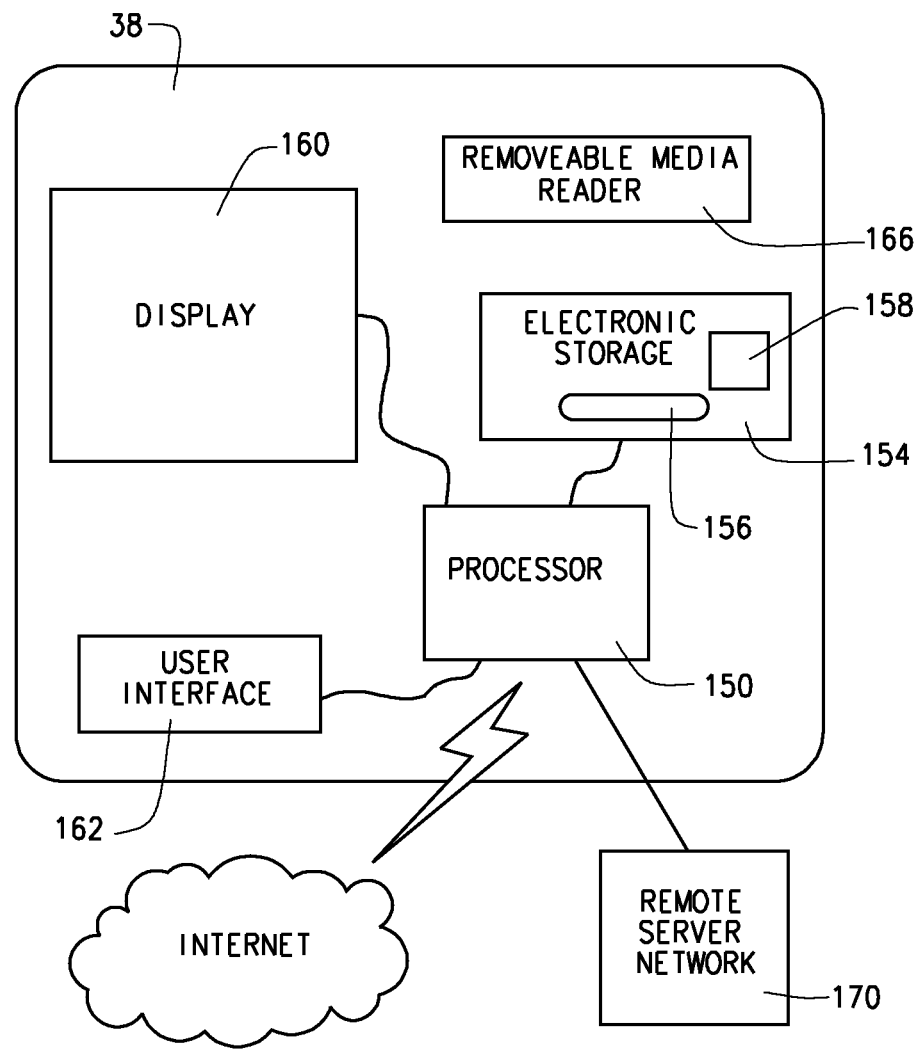
FIG. 8 is block diagram of a computer based control system of the PLR system shown in FIGS. 5 and 6, in accordance with various embodiments of the present disclosure.

Referring now to FIG. 8, in various embodiments, the system controller 38 is a computer based system that generally includes at least one processor 150 suitable to execute the PLR software, i.e., the various PLR programs and algorithms, to automatically, or robotically, control the operation of the PLR system 10, as described herein. The system controller 38 additionally includes at least one electronic storage device 154 that comprises a computer readable medium, such as a hard drive or any other electronic data storage device for storing such things as software packages or programs and algorithms 156 (e.g., the PLR software), and for storing such things as digital information, data, look-up tables, spreadsheets and databases 158. Furthermore, the system controller 38 includes a display 160 for displaying such things as information, data and/or graphical representations, e.g., the real-time streaming subject eye location data/images, and at least one user interface device 162, such as a keyboard, mouse, stylus, and/or an interactive touch-screen on the display 158.

In various embodiments the system controller 38 can further include a removable media reader 166 for reading information and data from and/or writing information and data to removable electronic storage media such as floppy disks, compact disks, DVD disks, zip disks, flash drives or any other computer readable removable and portable electronic storage media. In various embodiments the removable media reader 166 can be an I/O port of the system controller 38 utilized to read external or peripheral memory devices such as flash drives or external hard drives. In various embodiments, the system controller, i.e., the processor 150 can be communicatively connectable to a remote server network 170, e.g., a local area network (LAN), via a wired or wireless link. It should be understood that although the system controller 38 has sometimes been described herein as directly controlling the various automated, or robotic, operations of the PLR system 10, it is execution of the PLR software and other system control software, programs and/or algorithms by the processor 150, using inputs from the user interface 162 and various other components, sensors, systems and assemblies of the PLR system 10 that actually control the various automated, or robotic, operations of the system 10 described herein.

Figure 9:
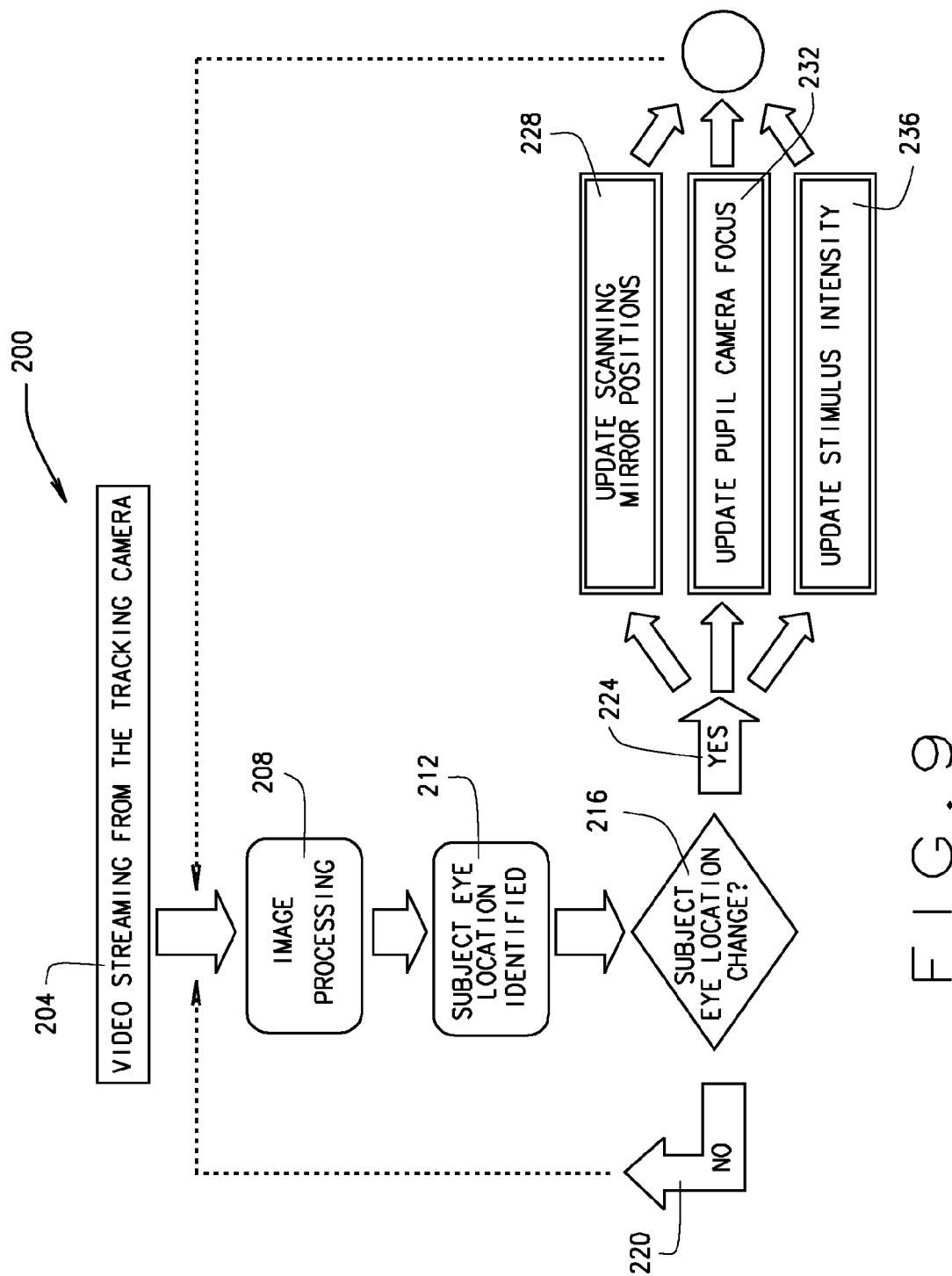
FIG. 9 is a flow chart illustrating the head movement tracking process executed by the PLR system shown in FIGS. 5 and 6, in accordance with various embodiments of the present disclosure.

Referring now to FIG. 9, FIG. 9 provides a flow chart 200 illustrating the operation of the PLR system 10, via execution of the PLR software, during the head movement tracking and pupil camera line-of-sight adjustment process described above. As described above, in operation, the PLR system 10 is located remotely (e.g., one-third of a meter or greater) from the subject 14, e.g., an infant or small child, and activated. Upon activation, the attention stimulus device 50 begins to display a movie or other viewable attraction, e.g., a video. The subject 14 can be positioned in a supine position, seated on a parent's lap or disposed in any other comfortable position where the subject 14 is free to move while viewing the viewable attraction.

Once the subject 14 has assumed his/her position the distance D from the PLR system 10, the tracking camera 18 begins to stream real-time subject eye location data to the system controller 38, as illustrated at 204. The streaming subject eye location data is processed, via execution of the PLR software, to identify the location of the subject's 14 eyes within the field of view of the tracking camera 18, as indicated at 208 and 212. The real-time streaming eye location data is continuously processed to continuously locate the subject's 14 eyes within the field of view of the tracking camera 18. More importantly, the real-time streaming eye location data is continuously processed to determine if the location of the subject's 14 eyes within the field of view of the tracking camera 18 changes, resulting from the subject 14 moving his/her head, as indicated at 216. If no change in eye location is identified, the PLR system simply continues to stream and process the real-time eye location data, as indicated at 220. However, if it is determined that the location of the subject's 14 eyes within the space of the video has changed, i.e., the subject 14 has moved his/her head, then the system controller 38 communicates with the scanning mirror controllers 54 and/or the auto-focus mechanism of the pupil camera(s) 22 and/or the optical stimulation light source 34, as indicated at 224. Subsequently, the new eye location is recorded and stored.

More particularly, if execution of the PLR software, using the streaming eye location data from the tracking camera 18, determines that the subject's eye location within the tracking camera 18 field of view has changed in a side-to-side manner, then the system controller 38 communicates with the scanning mirror controllers 54 to adjust the angle/position of the scanning mirrors 26 to maintain the on-axis line-of-sight between the subject's 15 pupils and the pupil camera(s) 22, as indicated at 228. Additionally, if execution of the PLR software, using the streaming eye location data from the tracking camera 18, determines that the subject's eye location within the tracking camera 18 field of view has changed in a front-to-back manner, (i.e., the distance D has changed), then the system controller 38 communicates with the auto-focus mechanism of the pupil camera(s) 22 to adjust the focus of the pupil camera(s) 22 to maintain the high resolution focus of the pupil camera(s) 22, e.g., a resolution of 50 µm or better, as indicated at 232. Furthermore, if front-to-back eye location movement is detected, the system controller will communicate with the power meter of the optical stimulation light source 34 to adjust the intensity setting to accommodate the change in eye location, as indicated a 236.

Figure 10:
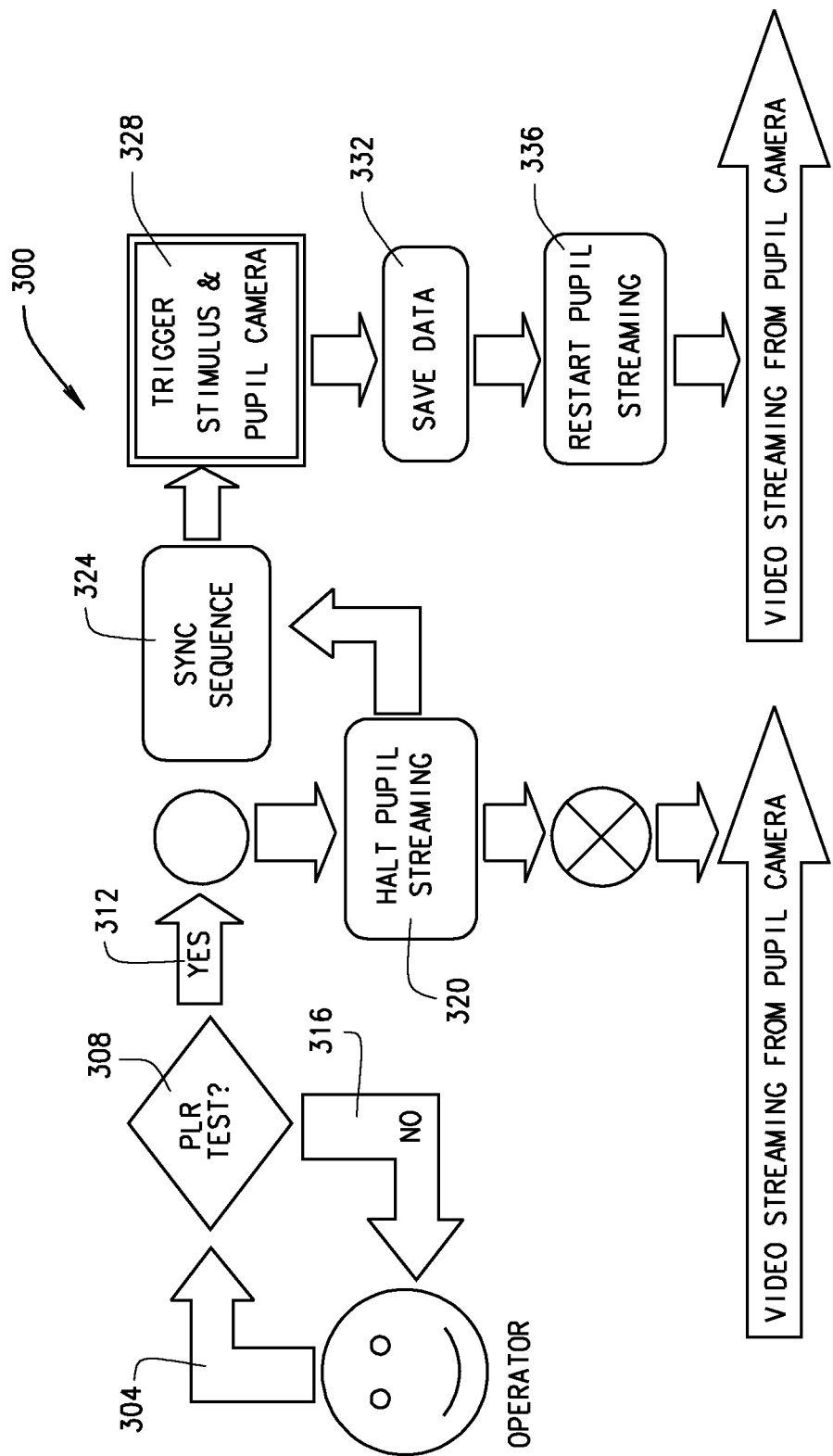
FIG. 10 is a flow chart illustrating a PLR testing initiation and testing sequence employed using the PLR system shown in FIGS. 5 and 6, in accordance with various embodiments of the present disclosure.

Referring now to FIG. 10, FIG. 10 provides a flow chart 300 illustrating the operation of the PLR system 10, via execution of the PLR software, once the system operator 58 initiates a PLR testing sequence. As described above, during the real-time streaming of the eye observation data from the pupil camera(s) 22, the eye observation data is rendered on the system controller display 160 as images of the subject's 14 eyes. Hence, the system operator 58 can observe the movement, or fixation, of the subject's 14 eyes, as indicated at 304, and determine whether or not to initiate a PLR testing sequence, as indicated at 308. If the system operator 58 observes that the subject's 14 eyes are relatively still, i.e., the subject's 14 eyes are not actively or frequently moving and the subject 14 appears to be relatively calm, at rest and focused on the viewable attraction displayed on the attention stimulus device 50, the system operator 58 can initiate a PLR test sequence, as indicated at 312. Otherwise, the system operator 58 continues to monitor the location of subject's 14 eyes within the tracking camera 18 field of view, as indicated at 316. The system operator 58 can initiate the PLR test sequence using any suitable means, e.g., depression of a key of the user interface 162 or the depression of a manual foot switch.

Once the system operator 58 initiates a PLR test sequence, as indicated at 312, execution of the PLR software temporarily stops the real-time streaming of the eye observation data from the pupil camera(s) 22, as indicated at 320, to set a starting point for acquiring the pupil stimulus/response data, i.e., to set a starting point for the acquisition of pupilography data. Subsequently, execution of the PLR software will synchronize the activation of the optical stimulation light source 34 and the starting of the streaming of the pupil stimulus/response data from the pupil camera(s) 22, such that the streaming of the pupil stimulus/response data begins slightly before, e.g., 0.5-1.0 seconds, the activation of the optical stimulation light source 34, as indicated at 324. Execution of the PLR software then initiates the streaming of the pupil stimulus/response data from the pupil camera(s) 22 and after a selected delay, e.g., 0.5-1.0 seconds, then triggers the optical stimulation light source 34 for a specific length of time, e.g., 0.5 seconds, as indicated at 328.

For example, in various embodiments, the pupil stimulus/response data streaming and optical stimulation can be synchronized by two TTL signals such that the acquisition of the pupil stimulus/response data will start 0.5 sec earlier than the optical stimulation pulse so that a 0.5 sec baseline pupil stimulus/response data can be acquired. In such exemplary embodiments, the optical stimulation can be controlled to flash for 100ms, and the pupil camera(s) 22 can continue to acquire and save the pupil stimulus/response data for 2.5 sec.

Upon initiation of the streaming of the pupil stimulus/response data, the system controller 38 begins saving the stimulus/response data, which contains image data of subject's 14 pupils before, during and after triggering of the optical stimulation light source 34, as indicated at 332. That is, the system controller 38 acquires and saves image data regarding the pupillary light reflex of the subject 14. Subsequently, the system controller 38 continues saving the stimulus/response data and triggers a sequence of optical stimulations, via the optical stimulation light source 34, to acquire and save a sequence of pupil stimulus/response data, i.e., a sequence of pupillary light reflex data. Once the sequence of optical stimulations and the corresponding acquisition of the pupil stimulus/response data is complete, execution of the PLR software restarts the real-time streaming of the eye observation data, as indicated at 336. Thereafter, the system operator 58 can observe the streaming eye observation data and selectively initiate subsequent episodes of PLR tests. In various implementations, one PLR test episode can take approximately 3.0 seconds and multiple episodes are completed within a 5 to 10 minute period to provide a complete assessment of PLR profiles. Meanwhile, the system controller 38 saves the subject's head position, orientation and gaze direction, which are used to correct the calculated pupil size.

Furthermore, execution of the PLR software analyzes the acquired and saved pupil stimulus/response data and generates: one or more pupilograms, such as that exemplarily illustrated in FIG. 1; and data and/or a graphical illustration regarding PLR latency and relative constriction amplitude of the subject's 14 pupillary response to the optical stimulations, such as that exemplarily illustrated in FIGS. 2A and 2B. For example, in various implementations, execution of the PLR software will automatically compute the pupillary response, i.e., the change in pupil size resulting from the optical stimulus provided by the optical stimulation light source 34. Briefly, the pixels located at the pupil boundary in each image will be determined using a k-mean-based segmentation method. A fast elliptic fitting algorithm of the PLR software will then be applied to fit the extracted pupil boundary, and the pupil area will be calculated as the area of the fitted ellipse. An average pupil diameter can be computed by approximating the pupil area as a circle. The pupil area is then corrected based the subject's distance, head orientation, and gaze direction to compute the actual pupil size. Once the pupil size is calculated from each image, the pupillogram is obtained. As illustrated in FIG. 2. the following basic PLR parameters will be measured for each measurement; initial pupil diameter, maximal construction diameter, PLR latency, constriction time, recovery time, construction velocity and recovery velocity. Additionally, the mean value of each PLR parameter can be calculated at all stimulus conditions. The final assessment is provided as a probability number based on known clinical data that indicates the likelihood of the subject 14 being developmentally delayed.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A pupillary light reflex system, said system comprising:
   a remote tracking and imaging system that is structured and operable to generate and acquire high resolution pupil stimulus and response data from a test subject while the test subject's head is moving and the test subject is disposed a distance from the remote tracking and imaging system that is at least one-third of a meter, wherein the remote tracking and imaging system comprises:
      a subject movement tracking camera structured and operable to continuously track 3-dimensional and rotational movement of the test subject's head within a field of view of the subject movement tracking camera to acquire subject eye location data regarding movement of a location of the subject's eyes within a field of view of the subject movement tracking camera;
      an optical stimulation device structured and operable to generate light that causes a pupillary response of the test subject's eyes; and
      at least one pupil data acquisition camera structured and operable to acquire the high-resolution pupillary stimulus and response data; and
   a computer based system controller that is structure and operable to execute pupillary light reflex (PLR) software to control the operation of the remote tracking and imaging system and compute PLR information based on the pupil stimulus and response data acquired as the test subject is moving, and to correct a measured pupil size based on the subject's head position, orientation and eye gaze direction.

2. The system of claim 1, wherein the remote tracking and imaging system further comprises:
   a plurality of movable scanning mirrors that are structured and operable direct a line-of-sight of each pupil data acquisition camera(s) toward the test subject's pupils; and
   a plurality of scan controllers connected to the scanning mirrors and structured and operable to continuously adjust an angle of the scanning mirrors to maintain an on-axis line-of-sight of the pupil data acquisition camera(s) with subject's pupils as the subject moves his/her head.

3. The system of claim 2, wherein the remote tracking and imaging system further comprises a subject illumination device that is structured and operable to project light toward the subject that is off-axis from the line-of-sight of pupil data acquisition camera(s), wherein the projected light from the subject illumination device is used as an illumination source for the subject movement tracking camera and the pupil data acquisition camera(s).

4. The system of claim 3, wherein the subject illumination device is structured and operable to project infrared light having a wavelength of approximately 800-900 nm.

5. The system of claim 2, wherein the optical stimulation device is structured and operable to generate green light having a wavelength of approximately 500-550 nm.

6. The system of claim 1, wherein the PLR information computed based on the pupil stimulus and response data acquired when the test subject is disposed a distance of at least one-third of a meter from the remote tracking and imaging system and is moving comprises pupil latency information.

7. The system of claim 1, wherein the remote tracking and imaging system is further structured and operable to generate and acquire the high resolution pupil stimulus and response data having a resolution of 50 μm or better.

8. A method for acquiring pupillary light reflex information from a test subject that moving, said method comprising:
- disposing a test subject at least one-third of a meter from a remote tracking and imaging system and such that the test subject is free to move and rotate his/her head in any direction;
- continuously tracking, via a subject movement tracking camera of the remote tracking and imaging system, 3-dimensional and rotational movement of the test subject's head within a field of view of the subject movement tracking camera;
- acquiring, via the tracking of the movement of the test subject's head, subject eye location data regarding movement of a location of the subject's eyes within a field of view of the subject movement tracking camera while the test subject is at least one-third of a meter from the remote tracking and imaging system and free to move his/her head;
- acquiring, via at least one pupil data acquisition camera of the remote tracking and imaging system, high-resolution eye observation data while the test subject is at least one-third of a meter from the remote tracking and imaging system and free to move his/her head;
- continuously adjusting an angle of a plurality of scanning mirrors to maintain an on-axis line-of-sight of the pupil data acquisition camera(s) with subject's pupils as the subject moves his/her head while the test subject is at least one-third of a meter from the remote tracking and imaging system and free to move his/her head;
- selectively triggering, based on the eye observation data, an optical stimulation device of the remote tracking and imaging system to generate an optical stimulus light that causes a pupillary response of the test subject's eye while the test subject is at least one-third of a meter from the remote tracking and imaging system and free to move his/her head;
- acquiring, via the pupil data acquisition camera(s), high resolution pupil stimulus and response data regarding a response of the test subject's pupils to the optical stimulus light while the test subject is at least one-third of a meter from the remote tracking and imaging system and free to move his/her head;
- continuously recording the subject's head position and orientation, and eye gaze direction during the acquisition of the high resolution pupil stimulus and response data;
- computing, via a computer based system controller of the remote tracking and imaging system, pupillary light reflex (PLR) information based on the pupil stimulus and response data while the test subject is at least one-third of a meter from the remote tracking and imaging system and free to move his/her head; and
- correcting a measured pupil size based on subject's head position and orientation, and eye gaze direction.

9. The method of claim 8 further comprising projecting, via a subject illumination device of the remote tracking and imaging system, light toward the subject that is off-axis from the line-of-sight of pupil data acquisition camera(s), wherein the projected light from the subject illumination device is used as an illumination source for the subject movement tracking camera and the pupil data acquisition camera(s).

10. The method of claim 9, wherein:
- projecting the off-axis light toward the subject comprises projecting off-axis infrared light having a wavelength of approximately 800-900 nm; and
- selectively triggering the optical stimulation device to generate an optical stimulus light comprises selectively triggering the optical stimulation device to generate a green optical stimulus light having a wavelength of approximately 500-550 nm.

11. The method of claim 8, wherein computing the pupillary light reflex (PLR) information comprises computing pupil latency information.

12. The method of claim 8, wherein acquiring the high resolution pupil stimulus and response data comprises acquiring pupil stimulus and response data having a resolution of 50 μm or better.

* * * * *